(12) United States Patent
Gallein

(10) Patent No.: US 7,199,576 B2
(45) Date of Patent: Apr. 3, 2007

(54) APPARATUS FOR TESTING PROCESSING ELECTRONICS

(75) Inventor: Dieter Gallein, Rosstal (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/191,999

(22) Filed: Jul. 29, 2005

(65) Prior Publication Data

US 2006/0103370 A1    May 18, 2006

(30) Foreign Application Priority Data

Oct. 18, 2004  (DE) ............ 10 2004 050 615

(51) Int. Cl.
*G01R 31/28* (2006.01)

(52) U.S. Cl. .................................... 324/158.1

(58) Field of Classification Search .............. None
See application file for complete search history.

(56) References Cited

U.S. PATENT DOCUMENTS

| | | | | |
|---|---|---|---|---|
| 4,622,515 A | * | 11/1986 | Everson | ............ 324/767 |
| 4,764,970 A | * | 8/1988 | Hayashi et al. | ............ 382/149 |
| 4,914,378 A | * | 4/1990 | Hayashi et al. | ............ 324/696 |
| 5,122,661 A | | 6/1992 | Kruszewski | |
| 5,510,723 A | * | 4/1996 | Canella et al. | ............ 324/758 |
| 5,517,111 A | * | 5/1996 | Shelor | ............ 324/235 |
| 6,218,910 B1 | * | 4/2001 | Miller | ............ 333/33 |
| 6,528,988 B2 | * | 3/2003 | Bolda et al. | ............ 324/202 |
| 6,614,237 B2 | * | 9/2003 | Ademian et al. | ............ 324/601 |
| 2004/0085076 A1 | * | 5/2004 | Lubcke et al. | ............ 324/609 |

OTHER PUBLICATIONS

IEEE Std 301-1988: "IEEE Standard Test Procedures for Amplifiers and Preamplifiers for Semiconductor Radiation Detectors for Ionizing Radiation", 1989.

* cited by examiner

*Primary Examiner*—Ha Tran Nguyen
*Assistant Examiner*—Richard Isla-Rodas
(74) *Attorney, Agent, or Firm*—Harness, Dickey & Pierce, P.L.C.

(57) ABSTRACT

An apparatus is disclosed for testing the processing electronics of a detector module for an X-ray computer tomograph. To provide a measurement environment which is as noise-free as possible, the processing electronics to be tested are tested when they are DC decoupled from a current source and a measurement and tapping apparatus.

15 Claims, 3 Drawing Sheets

APPARATUS FOR TESTING PROCESSING ELECTRONICS

The present application hereby claims priority under 35 U.S.C. §119 on German patent application number DE 10 2004 050 615.9 filed Oct. 18, 2004, the entire contents of which is hereby incorporated herein by reference.

FIELD

The invention generally relates to an apparatus for testing processing electronics, particularly to an integrated circuit as part of a detector module for an X-ray computer tomograph.

BACKGROUND

The development of detector modules for X-ray computer tomographs is characterized by constant miniaturization of the detector elements used for detecting the X-ray radiation. In the meantime, the X-ray radiation is detected using "detector arrays", which currently comprise 64 rows of detector elements, for example. Each row in turn has a multiplicity of detector elements situated next to one another.

As a result of the miniaturization of the detector elements, the signals generated thereby also become smaller. It is necessary particularly to amplify the signals using downstream processing electronics. To ensure the highest possible image quality, it is necessary for the further processing of the signals by the processing electronics to be exact. To rule out errors to this extent, the quality of the processing electronics is examined before the detector array is assembled.

In this case, however, the problem arises that measurement of an integrated circuit or processing electronics is extremely sensitive to noise. To date, there has been no reliable success in providing a suitable low-noise measurement environment which can be used to test the quality of the processing electronics. There is also currently no known simple design of apparatus for testing the processing electronics which can be used to test a plurality of channels provided for the processing electronics simultaneously.

SUMMARY

It is an object of at least one embodiment of the present invention to reduce or even eliminate at least one of the drawbacks based on the prior art. In particular, one aim of at least one embodiment is to specify an apparatus which allows exact testing of processing electronics, particularly of the processing electronics in a detector module for an X-ray computer tomograph. In accordance with a further aim of at least one embodiment of the invention, the aim is to be able to test as many channels of the processing electronics as possible simultaneously.

This object is achieved by the features of claim 1. Expedient refinements of the invention can be found in the features of claims 2 to 14.

At least one embodiment of the invention provides an apparatus for testing processing electronics having a current source which has a power supply and a test current generation device for generating a test current, the power supply and the test current generation device being connected by a first galvanically isolated coupler, a contact apparatus, connected downstream of the test current generation device, for making contact with first contacts provided on the processing electronics, a tapping apparatus for making contact with second contacts provided on the processing electronics, and a downstream measurement and evaluation apparatus for measuring and evaluating the signals tapped off at the second contacts, the second contact apparatus and the measurement and evaluation apparatus being connected by a third galvanically isolated coupler.

"Processing electronics" within the meaning of the present invention is to be understood to include an integrated circuit, a module including a plurality of integrated circuits and the like. The integrated circuit(s) may be accommodated on a circuit board which is provided with the first and second contacts, for example.

The proposed apparatus allows reliable and exact testing of high-resolution processing electronics, particularly of the processing electronics in a detector module for an X-ray computer tomograph. As a result of the proposed galvanic isolations by the first and third galvanically isolated couplers between the power supply and the first contact apparatus— on the one hand—and the second contact apparatus and the measurement and evaluation device—on the other hand—an extremely low-noise measurement environment is produced for the processing electronics which are to be tested. Noise, drift or linearity errors are kept so small that they are negligible during the measurement. The proposed apparatus can be used to measure currents in the femtoamp to microamp range.

The processing electronics can have a plurality of channels. In accordance with one advantageous refinement, the first contact apparatus has a contact element, preferably a spring-loaded contact pin, preferably for each channel which is to be tested. The contact pin may be made from gold, for example. The proposed first contact apparatus allows simple and low-wear contact to be made with the processing electronics. The contact elements can form a contact array which is designed to correspond to a further contact array provided on the processing electronics.

At least one embodiment is particularly suitable for testing processing electronics which include one or more integrated circuits and in which the further contact array is provided for connection to a detector array for detecting X-rays in the field of computer tomography. Such a detector array includes a multiplicity of detector elements. For each detector element, the processing electronics may contain a separate channel for processing the signals delivered thereby. It is readily possible to provide a large number of contact pins, for example more than 1000, on the contact apparatus in order to test more than 1000 channels of the processing electronics simultaneously. To this end, the further contact array merely needs to be pushed with a prescribed pressure onto a contact pin array, formed from a multiplicity of contact pins, on the contact apparatus.

In accordance with one further refinement of at least one embodiment, the contact element is connected to the power supply via a precision resistor. If a plurality of contact elements are provided, each of the contact elements is connected to the power supply via a precision resistor. The precision resistor(s) is/are expediently held in a first housing. The contact apparatus may likewise be provided on the first housing.

The second contact apparatus is advantageously provided on a second housing which is arranged so as to be physically separate from the first housing. The proposed separate arrangement of the two housings contributes to reducing or even minimizing the disturbing parallel-path currents between the analog and digital components.

In respect of the handling of the inventive apparatus, it has been found to be expedient for a distance between the first housing and the second housing to be proportioned such that the first contact apparatus and the second contact apparatus can make direct contact with the processing electronics to be tested. The processing electronics are normally held on a narrow rectangular circuit board, one end of which has the contact array and the other end of which has contacts for tapping off the output signals.

In the case of at least one proposed embodiment, the processing electronics, having been inserted into the apparatus, form a bridge between the first and second housings, with the further contact array of the processing electronics being connected to the contact array, formed from the first contacts, of the contact apparatus on the first housing. Further contacts, provided at the other end of the circuit board for the processing electronics, for tapping off the signals are connected to the second contacts provided on the second housing.

The measurement and evaluation device may include a suitably converted personal computer, for example. In accordance with a further refinement, the measurement and evaluation device may include a control device for controlling the current source. The control device is also expediently galvanically isolated from the test current generation device.

To provide an operating voltage for the processing electronics, a further current source may be provided which has a further power supply and an operating voltage generation device, which is DC isolated therefrom, for generating the operating voltage. In this case too, the measurement and evaluation device may include a further control device for controlling the operating voltage generation device. The further control device is also expediently galvanically isolated from the operating voltage generation device.

Magnetic and/or optical couplers may be provided for the galvanic isolation. Such couplers may be integrated in the measurement and evaluation device, in the current source and in the further current source.

The processing electronics may be part of a detector module for an X-ray computer tomograph, in particular. To test such processing electronics, a detector array has not yet been assembled. A further contact array provided for making contact with the detector array has contact made by the first contact elements of the first contact apparatus. Each channel of the processing electronics is tested by applying a prescribed test current and subsequently evaluating an output signal generated thereby.

To test processing electronics in large numbers, the proposed apparatus may also be part of an automated test device. In this case, a robot may be provided for automatically supplying and removing processing electronics to be tested for the first contact apparatus and second contact apparatus. The robot can be used to grip the processing electronics and to push them onto the first contact apparatus and second contact apparatus for the duration of the test in order to make electrical contact. It is then possible to reject processing electronics which do not satisfy prescribed quality characteristics.

To ensure the simplest possible accessibility and contact-making, it is advantageous to provide both the first contact apparatus and the second contact apparatus on a respective top side of the first and second housings, specifically such that the respective first contact areas of the contact apparatus and second contact apparatus are at the same level.

BRIEF DESCRIPTION OF THE DRAWINGS

An exemplary embodiment of the invention will be explained in more detail below with reference to the drawings, in which.

DETAILED DESCRIPTION OF THE EXAMPLE EMBODIMENTS

Figure 1:
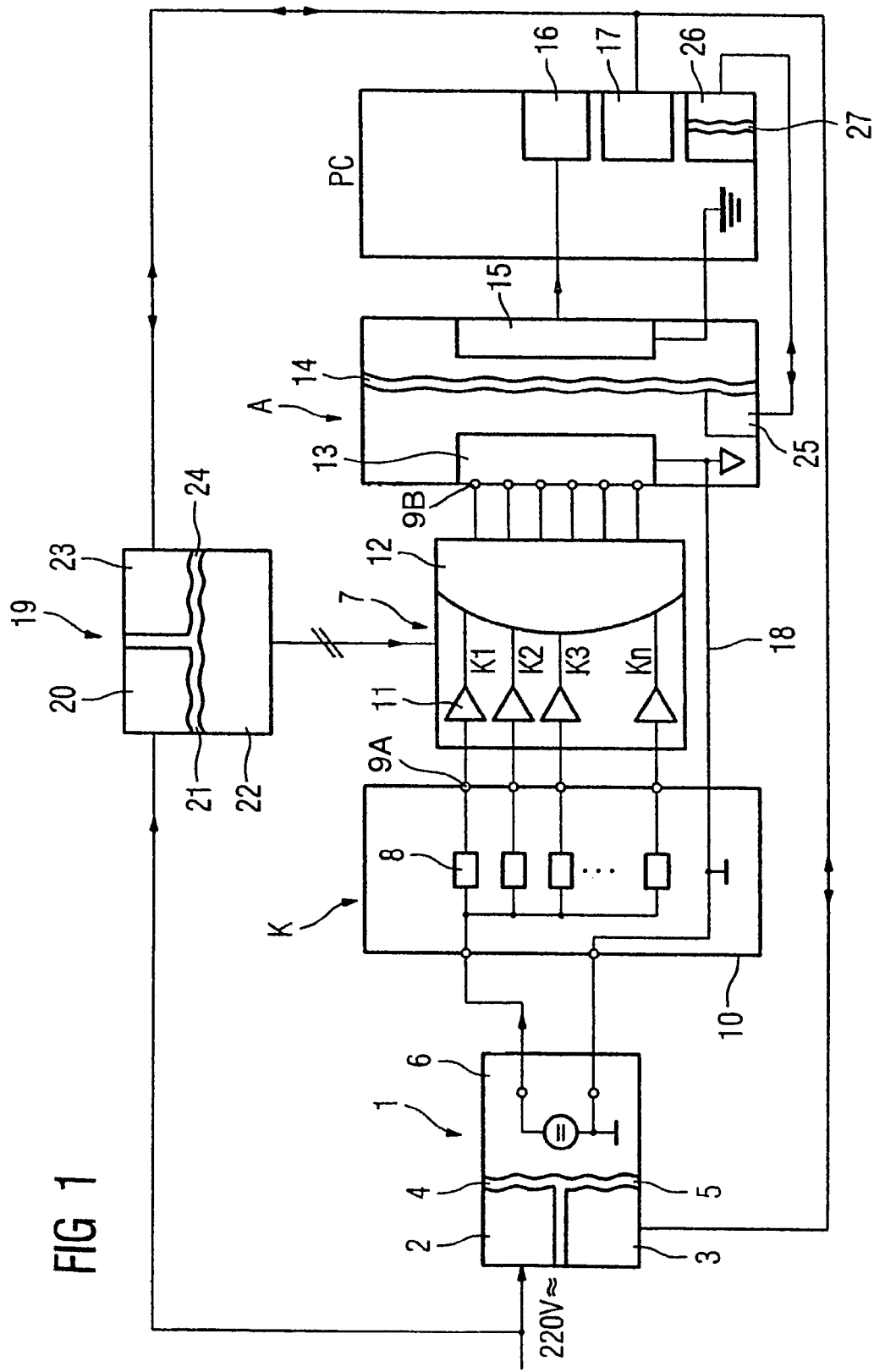
FIG. 1 shows a schematic overview of the fundamental components of the apparatus.

FIG. 1 shows the fundamental components of the apparatus. A current source, denoted generally by the reference symbol 1, has a power supply 2 and a first actuation device 3. The power supply 2 and the first actuation device 3 are isolated by way of a first galvanically isolated coupler and a second galvanically isolated coupler, respectively, from a test current generation device 6 which provides a suitable prescribed current for testing a test object denoted generally by the reference symbol 7. The test object 7 may be an integrated circuit, a module including a plurality of integrated circuits and the like. The test object 7 could be part of a detector module for an X-ray computer tomographer 7A.

The test current or the test voltage is applied to first contacts 9A via precision resistors 8. The first contacts 9A form a contact array (not shown here) which is designed to correspond to a further contact array, provided on the test object 7, for connecting a detector array (not shown here). The first contacts 9A or the contact array formed therefrom are mounted with a first contact apparatus K on a first housing 10, which also holds the precision resistors 8. The test object 7 has a multiplicity of channels K1, K2, K3, . . . , Kn. Each of the channels K1, K2, K3, . . . , Kn is provided with an amplifier 10.

In addition, the test object 7 has an analog/digital converter 12 which can be used to convert the analog signals supplied into digital output signals. To tap off the output signals, a second contact apparatus A is provided which has a female connector 13 for making contact with second contacts 9B of the test object 7. Instead of the female connector 13, it is naturally also possible for other suitable contact device(s) to be provided, for example a male connector or—in a similar manner to at the input, a further contact array formed from a multiplicity of further contact pins.

The signals tapped off are transmitted in the second contact apparatus A across a third galvanically isolated coupler 14 to a downstream converter logic unit 15 in which the signals supplied are converted. From there, the converted signals are passed to a personal computer PC which is provided with a data capture device 16 for capturing the data transmitted by the converter logic unit 15. The personal computer PC is also provided with a controller 17 which can be used to actuate the first actuation device 3 in the current source 1. It is thus possible to set the test signals required for testing the test object 7.

A ground connection 18 connecting the test current generation device 6 to the first contact apparatus K and to the second contact apparatus A is only extremely thin, particularly between the first contact apparatus K and the second contact apparatus A. As such, the parallel-path currents between an analog ground and a digital ground for the test object 7 are reduced or even minimized. The test object 7 is thus substantially decoupled from the first contact apparatus K and from the second contact apparatus A.

As is also clear from FIG. 1, the first contact apparatus K and the second contact apparatus A are fully galvanically isolated from the rest of the apparatus by means of the galvanically isolated couplers 4, 5 and 14. The proposed galvanically isolated couplers 4, 5 and 14 allow an extremely low-noise measurement environment which can be used to measure even currents in the femtoamp to microamp range.

To generate an operating voltage for the test object 7, a further current source 19 is provided which, like the current source 1, has a further power supply 20 which is isolated from an operating current generation device 22 by way of a fourth galvanically isolated coupler 21. A second actuation device 23 may likewise be connected to the controller 18. The second actuation device 23, which is used to set the operating voltage, is also galvanically isolated from the operating voltage generation device 22 by means of a fifth galvanically isolated coupler 24.

For the purpose of data interchange with the test object 7, the second contact apparatus A may have a third actuation device 25, which is connected to a further controller 26, provided in the measurement and evaluation apparatus PC, for the purpose of data interchange. The further controller 26 has a sixth galvanically isolated coupler 27. As such, the further controller 26 and the third actuation device 25 are also DC isolated, that is galvanically isolated, from one another.

Figure 2:
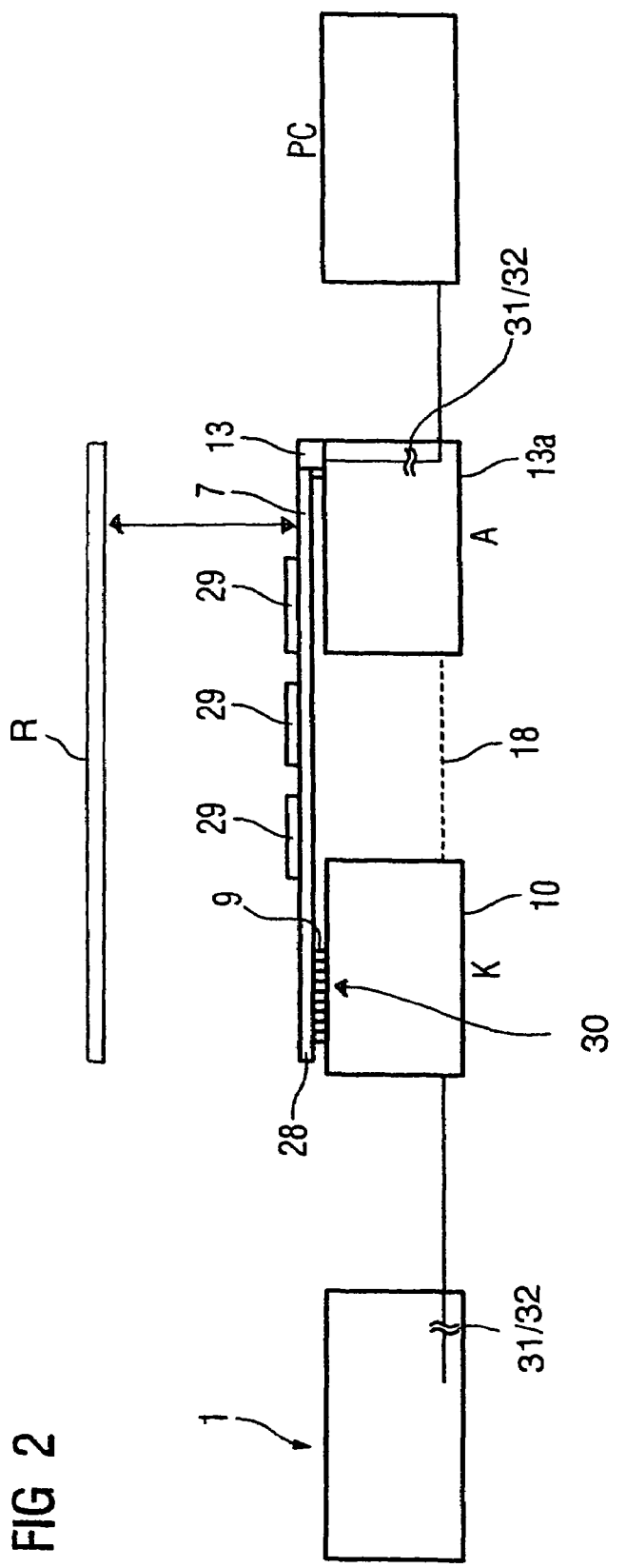
FIG. 2 shows a schematic side view of the first contact apparatus and second contact apparatus.

FIG. 2 shows a schematic side view of the apparatus. On the top side of the first housing 10, the first contact apparatus K has a contact array 30 or contact pin array which is formed from contact pins/elements (preferably spring-loaded pins) 9 and which may be in the form of a conventional press-fit connector. The test object 7 has a further contact array (not shown here) which is designed to correspond to the contact pin array and which is provided on an underside of a circuit board 28.

The circuit board 28, which is in elongate form here, holds integrated components (processing electronics) 29 which contain, by way of example, the amplifiers 11, the analog/digital converter 12 and the like. The second contact apparatus A has a second housing 13a. On a top side of the second housing 13a, there is the female connector 13, which is used to make contact with plug contacts (not shown here) provided at the other end of the circuit board 28.

The first housing 10 and the second housing 13a are arranged at a distance from one another. The distance is chosen such that contact with the first contact apparatus K and with the second contact apparatus A can be made by simply placing the test object 7 on top.

To make contact between the test object 7 and the first contact apparatus K and also the second contact apparatus A, there may also be adapters provided for alignment with differing geometries of the circuit board 28 holding the processing electronics and of the contact fields and the like provided thereon.

The current source used for testing an integrated circuit with a channel may be, by way of example, a commercially available measuring instrument from the firm Keithley, type 6430, Sub-Femtoamp Remote SourceMeter.

The proposed full galvanically decoupling of the test object 7 from the measurement environment counteracts the formation of parallel-path currents and other disturbances which corrupt the measurement result. The galvanically decoupling can be provided using conventional magneto-couplers 31 or optocouplers 32. The proposed apparatus can be used to test a multiplicity of channels K1, K2, K3, ..., Kn simultaneously.

A robot R could be provided for automatically supplying and removing processing electronics 7 to be tested for the first contact apparatus K and second contact apparatus A.

Figure 3A:
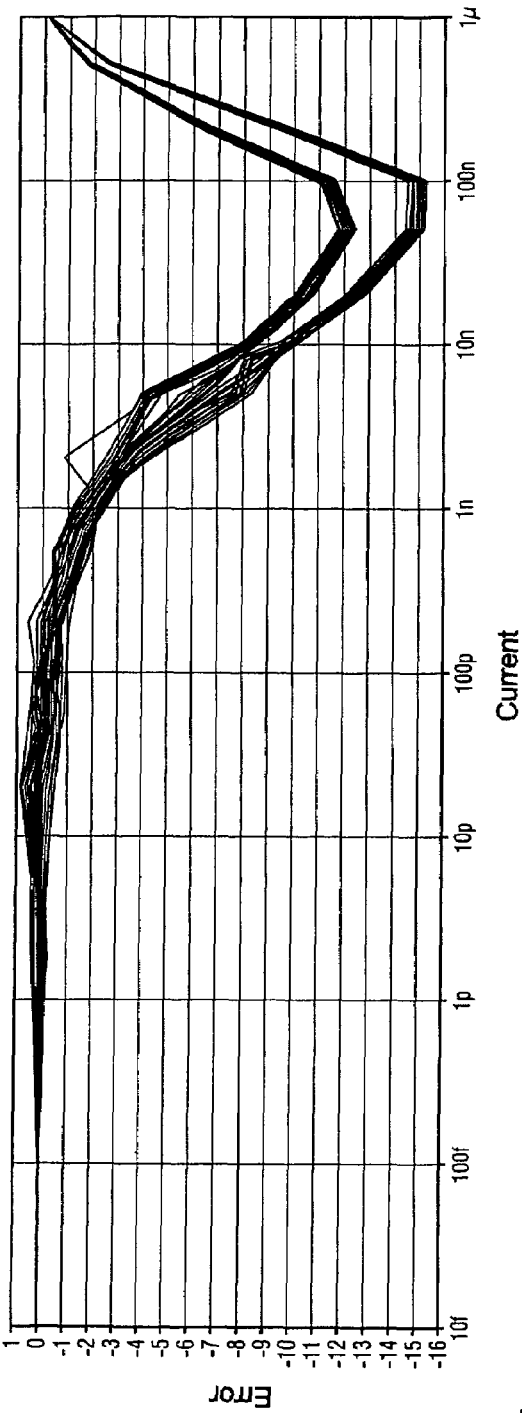
FIG. 3a shows the signal profile of tested channels as a function of the applied test current.
Figure 3B:
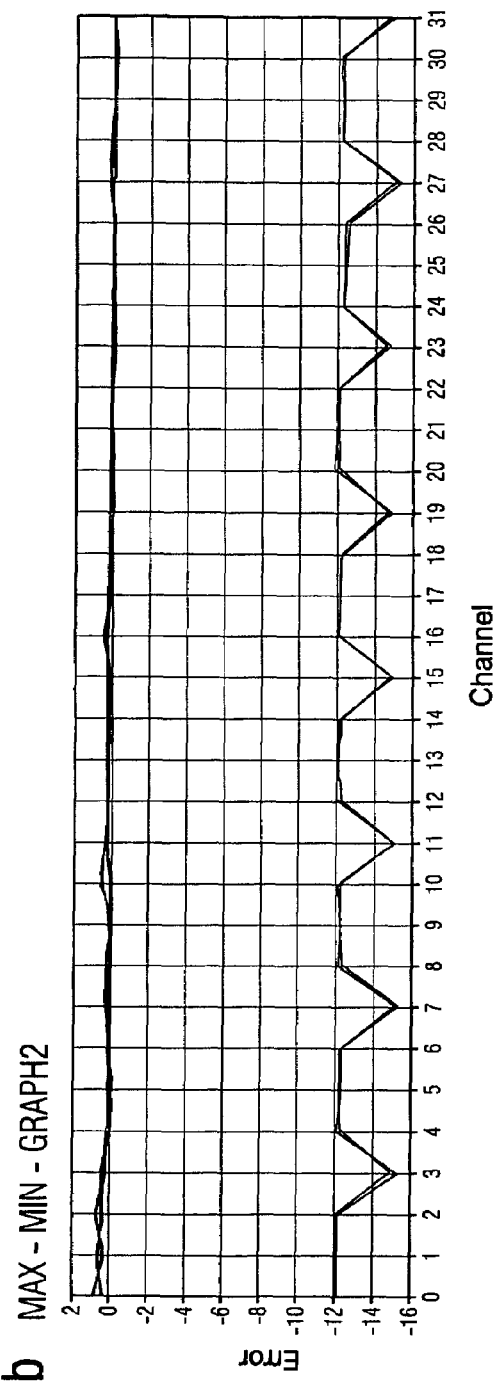
FIG. 3b shows the minimum and maximum errors in the tested channels.

FIGS. 3a and 3b show a typical test result. FIG. 3a shows a signal profile as a function of the applied test current for a multiplicity of channels K1, K2, K3, ..., Kn. From this, it is possible to see, by way of example, that from a test current of more than 100 pA upward there is an increase in an error in the tested processing electronics. The maximum for the error is a test current of approximately 100 nA. In addition, it may be seen from FIG. 3a that a first group of channels K1, K2, K3, ..., Kn has a smaller error than a second group of channels K1, K2, K3, ..., Kn.

FIG. 3b shows the maximum and minimum errors for each channel K1, K2, K3, ..., Kn. This immediately allows a statement to be made about the quality of each of the tested channels K1, K2, K3, ..., Kn.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for testing processing electronics, comprising:
   a current source including a power supply and a test current generation device for generating a test current, the power supply and the test current generation device being connected by a first galvanically isolated coupler;
   a first contact apparatus, connected downstream of the test current generation device, for making contact with first contacts provided on the processing electronics;
   a second contact apparatus for making contact with second contacts provided on the processing electronics; and
   a downstream measurement and evaluation apparatus, for measuring and evaluating the signals measured at the second contacts, the second contact apparatus and the measurement and evaluation apparatus being connected by a third galvanically isolated coupler.

2. The apparatus as claimed in claim 1, wherein the processing electronics have a plurality of channels.

3. The apparatus as claimed in claim 2, wherein the first contact apparatus has a contact element for each channel which is to be tested.

4. The apparatus as claimed in claim 3, wherein the contact elements form a contact array which is designed to correspond to a further contact array provided on the processing electronics.

5. The apparatus as claimed in claim 3, wherein the contact element is connected to the test current generation device via a precision resistor.

6. The apparatus as claimed in claim 5, wherein the precision resistor is accommodated in a first housing.

7. The apparatus as claimed in claim 6, wherein the first contact apparatus is provided on the first housing.

8. The apparatus as claimed in claim 6, wherein the second contact apparatus is provided on a second housing, arranged so as to be physically separate from the first housing.

9. The apparatus as claimed in claim 1, wherein a distance between the first housing and the second housing is proportioned such that the first contact apparatus and the second contact apparatus can make direct contact with the processing electronics to be tested.

10. The apparatus as claimed in claim 1, wherein the measurement and evaluation device includes a control device for controlling the test current generation device.

11. The apparatus as claimed in claim 10, wherein the control device is connected with the test current generation device by a sixth galvanically isolated coupler.

12. The apparatus as claimed in claim 1, wherein each of the galvanically isolated couplers is a magnetic or optical coupler.

13. The apparatus as claimed in claim 1, wherein the processing electronics are part of a detector module for an X-ray computer tomograph.

14. The apparatus as claimed in claim 1, wherein a robot is provided for automatically supplying and removing processing electronics to be tested to the first and second contact apparatus.

15. The apparatus as claimed in claim 3, wherein the contact element is a spring-loaded contact pin.

* * * * *